United States Patent [19]

Maul et al.

[11] Patent Number: 4,554,368

[45] Date of Patent: Nov. 19, 1985

[54] CONTINUOUS PROCESS FOR THE PREPARATION OF ALKYLTIN THIOCARBOXYLIC ACID ESTERS

[75] Inventors: Rudolf Maul, Lorsch; Hans Stephan, Bensheim; Walter Wolf, Lautertal, all of Fed. Rep. of Germany

[73] Assignee: Ciba-Geigy Corporation, Ardsley, N.Y.

[21] Appl. No.: 445,812

[22] Filed: Dec. 1, 1982

[51] Int. Cl.$^4$ .............................................. C07F 7/22
[52] U.S. Cl. ...................................................... 556/91
[58] Field of Search ...................................... 260/429.7

[56] References Cited

U.S. PATENT DOCUMENTS

| | | | |
|---|---|---|---|
| 2,752,325 | 6/1956 | Leistner et al. | 260/429.7 X |
| 2,832,750 | 4/1958 | Weinberg et al. | 260/429.7 |
| 2,832,751 | 4/1958 | Weinberg et al. | 260/429.7 X |
| 2,870,119 | 1/1959 | Leistner et al. | 260/429.7 X |
| 3,660,442 | 5/1972 | Ludwig | 260/429.7 |
| 4,104,292 | 8/1978 | Dworkin et al. | 260/429.7 |
| 4,193,913 | 3/1980 | Abeler | 260/429.7 X |
| 4,292,252 | 9/1981 | Collins et al. | 260/429.7 |

*Primary Examiner*—Helen M. S. Sneed
*Attorney, Agent, or Firm*—Harry Falber

[57] ABSTRACT

A process for the production of alkyltin thiocarboxylic acid esters from alkyltin halides and thiocarboxylic acid esters in the presence of an acid acceptor, which process comprises carrying out the reaction continuously in a reaction system comprising 1 to 5 agitator vessels with an average dwell time of 1 to 60 minutes, at a constant pH value in the range from 3 to 8, and in a temperature range from 40° to 80° C. and separating the product drawn off from the reaction system from the aqueous phase and subsequently drying it.

The alkyltin thiocarboxylic acid esters obtained by the process of the invention are used for stabilizing homo- and copolymers of vinyl chloride.

13 Claims, No Drawings

CONTINUOUS PROCESS FOR THE PREPARATION OF ALKYLTIN THIOCARBOXYLIC ACID ESTERS

Alkyltin thiocarboxylic acid esters are known stabilisers for homopolymers and numerous copolymers of vinyl chloride. Their preparation is described e.g. in Houben-Weyl, Methoden der Organischen Chemie, Vol. XIII/6 (1978), pp. 348–350. It is carried out by discontinuous reaction of alkyltin oxides or alkyltin halides, in particular alkyltin chlorides, with thiocarboxylic acid esters. The reaction with alkyltin chloride is preferably carried out in the presence of a base as acid acceptor, under different temperature, time and pH conditions.

The preparation of alkyltin thiocarboxylic acid esters from the corresponding alkyltin halides is normally carried out in the presence of an organic solvent, as described e.g. in U.S. Pat. No. 2 832 751. It is also known from the literature to carry out the reaction without a solvent (q.v. U.S. Pat. No. 3 716 568).

In the batchwise processes using an organic solvent, it is possible to carry out the reaction both at relatively low and at more elevated temperature. In this reaction, the aqueous phase is usually well and cleanly separated from the product phase.

The processes carried out without a solvent result in a higher space/time yield. Further, the step of regenerating the solvent is made redundant in these processes.

The essential drawbacks of the processes carried out with an organic solvent are that the space/time yield is drastically reduced and the solvent employed has to be removed by distillation in the working up phase, resulting in energy consumption and in spent air and waste water pollution. In addition, the flash point of the product falls sharply on account of solvent residues, so that greater safety measures are required in the plant.

On the other hand, the absence of a solvent in the solvent-free processes is a disadvantage, as usually a very poor separation of the organic product phase from the aqueous phase results. This means long standing times and also product loss through the formation of an intermediate phase. In addition, lengthy distillation times are required for the residual water because of the difficulty of separating it from the organic phase, with the consequence that the product is subjected to prolonged exposure to heat.

Low temperatures are necessary for the batchwise reaction of alkyltin halides with thiocarboxylic acid esters. The reaction is so strongly exothermic that the addition of base can only be made as quickly as the removal of heat through the reactor jacket permits, thus resulting in lengthy reaction times in large-scale production and, accordingly, in a lower space/time yield. Moreover, at the start of the addition of base the pH of the reaction mixture is in the strongly acid range (below pH 1) and then gradually rises to the neutral range. During the reaction in the acid range, undesirable saponification reactions may occur, e.g. of the thiocarboxylates, which impair the quality of the product. In addition, previous experience has shown that, in batchwise operation, the final pH value must be adjusted exactly, so that uniform production is only ensured by very careful monitoring. Exceeding the pH value results in diminished product quality and in product loss.

The reaction of alkyl tin oxides with e.g. thiocarboxylic acid esters necessitates the technically complicated intermediate isolation and drying of the alkyltin oxides. The process described in German Auslegeschrift 2 209 336 affords no advantages, as the thin-film process requires complicated reaction apparatus.

It is the object of the present invention to provide a continuous process for the preparation of alkyltin thiocarboxylic acid esters, which process makes it possible to react the reactants in simple apparatus with short dwell times, at constant pH and and in a wide temperature range, if desired without cooling or removing the heat of reaction and neutralisation, thereby eliminating the previously described drawbacks of the known processes.

Accordingly, the present invention relates to a process for the preparation of alkyltin thiocarboxylic acid esters from alkyltin halides and thiocarboxylic acid esters in the presence of an acid acceptor, which process comprises carrying out the reaction continuously in a system consisting of 1 to 5 agitator vessels with an average dwell time of 1 to 60 minutes, at a constant pH value in the range from 3 to 8, and in a temperature range from 40° to 80° C.

Surprisingly, it has been found that only in a continuous operation, as opposed to a discontinuous process, does no loss of quality occur, as the product is exposed to high temperatures only for a short time and at a constant pH value, preferably in the neutral range. Accordingly, it is possible to obtain products in a continuous process, e.g. at 75° C. and pH 6.5, without loss of quality and in substantially higher space/time yield. In addition, the desired pH range can be easily adjusted during the entire reaction. The process is carried out in a continuously operating reaction system consisting of 1 to 5 reaction vessels, preferably of two reaction vessels.

If the reaction is carried out in a two-stage agitator vessel cascade, the dwell time in the first vessel will be from 1 to 60 minutes, preferably from 1 to 10 minutes, but most preferably from 1 to 5 minutes. The vessels of the two-stage cascade may be of the same or different size. The dwell times in the individual reaction vessels will therefore correspondingly differ. The reaction temperature is in the range from 40° to 80° C., preferably from 50° to 60° C. By appropriate choice of temperature when charging the reaction vessels with the starting materials, it is also possible to carry out the reaction adiabatically. This is done by adding the starting materials continuously at low temperature, preferably in the range from 20° to 30° C. The heat of reaction and neutralisation need not be removed, so that cooling energy can be saved.

In the continuous operation of this invention, the pH range is kept between 3 and 8, preferably at a constant value between 5 and 7, during the entire reaction. The pH can be adjusted in simple manner, e.g. by a pH meter, with a base.

Suitable bases are: alkali metal hydroxides and alkaline earth metal hydroxides such as sodium, potassium or calcium hydroxide; alkaline earth oxides such as calcium oxide; and also ammonia or alkali metal carbonates such as sodium carbonate or potassium carbonate. They are preferably used in the form of 10 to 50% solutions. Particularly advantageous is e.g. 18 to 20% sodium hydroxide solution. However, tertiary amines such as triethylamine or pyridine may also be used, if desired.

It is preferred to carry out the reaction of this invention without an organic solvent. However, the reaction may also be carried out in the presence of an inert organic solvent. Examples of suitable solvents are aliphatic and aromatic hydrocarbons, ethers, esters and ketones, such as hexane, petroleum ether, toluene, xylenes, methyl isobutyl ketone or methyl acetate.

Various alkyltin thiocarboxylic acid esters may be prepared by the process of this invention. Particularly interesting compounds are those of the formula

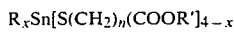

$$R_xSn[S(CH_2)_n(COOR')]_{4-x}$$

wherein x and n are 1 or 2, R is methyl, butyl, octyl, lauryl or the —CH$_2$CH$_2$COO—n—C$_4$H$_9$ group, and R' is a C$_8$–C$_{16}$alkyl group.

R as butyl may be n-butyl, isobutyl or tert-butyl, with n-butyl being preferred. R as octyl may be n-octyl or 2-ethylhexyl, with n-octyl being preferred.

R' may be e.g. straight chain or branched octyl, decyl, dodecyl, tetradecyl and hexadecyl, as well as the commercially available mixtures of alcohols known as alfols, which contain substantially alkyl groups having the same number of carbon atoms and are mainly branched. The alkyl groups are here known as "alfyls".

The starting materials employed for the process are alkyltin halides and thiocarboxylic acid esters. The alkyltin halides employed are chlorides, bromides or iodides, preferably alkyltin chlorides or bromides in an amount of 85 to 115 mole %, based on the thiocarboxylic acid esters. The thiocarboxylic acid esters are known compounds. Thioglycolic and thiopropionic acid esters are especially preferred.

The initiation of the continuous reaction is conveniently effected batchwise, beginning first with the addition of the reagents, then adding the aqueous solution of the base for adjusting the desired pH range, and finally adding both reaction components and the solution of the base continuously.

The starting alkyltin halides and thiocarboxylic acid esters may be added to the reactor at 20°–30° C. either as a previously prepared mixture or added separately at different temperatures.

The process of the invention may be carried out e.g. in the following system:

To initiate the reaction, the appropriate alkyltin chloride or chlorides and the corresponding thiocarboxylic acid ester are pumped in the required molar ratio into the reactor until this latter is about half full. With stirring, an aqueous solution of the base is then added until the desired pH value is reached, after which the continuous addition of the sodium hydroxide solution, the alkyltin chloride(s) and the thiocarboxylic acid ester is commenced with. When the controlled volume has been reached, the reaction mixture is pumped into the second reactor such that the controlled volume in the second agitator vessel is maintained.

After an average dwell time of 1 to 60 minutes preferably of 1 to 10 minutes and, most preferably, of 1 to 5 minutes, the reaction mixture is discharged continuously from the reactor in order to separate the organic phase from the aqueous phase. The separation of the water from the reaction mixture drawn off from the reactor is preferably effected by a continuously operating liquid-liquid extractor or else also by suitable separating columns.

Liquid-liquid extractors are conventional separators used in chemical engineering. Particulars on the individual extraction methods are to be found in Ullmann, Enzyklopädie der technischen Chemie, Vol. 2, 4th edition (1972), on page 553, and a description of the individual apparatus and extractors will be found on pp. 560–564. The continuously operating liquid-liquid centrifugal extractor is particularly advantageous for separating water from the reaction mixture drawn off from the reactor, preferably at 40°–50° C.

The so isolated product phase may conveniently also be dried continuously, e.g. by continuous spray drying or also with the aid of a thin-film or falling film evaporator.

Spray drying, thin-film or falling film evaporators are also known drying or evaporating systems. Such equipment is described e.g. in Ullmann, Enzyklopädie der technischen Chemie. Vol. 2, 4th Edition (1972) on pp. 712–713 (spray driers) and on pp. 655–656 (thin-film and falling film evaporators).

The following Examples describe the invention in more detail.

EXAMPLE 1

100 parts by weight of a mixture of 30 mole % of mono-n-octyltin trichloride and 70 mole % of di-n-octyltin dichloride together with 104 parts by weight of 2-ethylhexyl thioglycolate are pumped continuously at a temperature of 60° C. into a reactor system comprising a cascade of two reactors each equipped with stirrer, level meter, pH meter and thermometer. With efficient stirring, aqueous sodium hydroxide solution is simultaneously added to the reaction mass such that a pH of 6.5–7.0 is maintained in the first reactor. The addition or sodium hydroxide is controlled by the pH meter in the first reactor. The reaction mixture is pumped into the second reactor, the volume being controlled by the level meter. Feed and discharge of the reaction mixture are controlled such that the dwell time of the reaction mass in the first reactor is 5 minutes. The heat of reaction liberated during the reaction is removed such that a constant temperature of 60° C. is kept in the first and in the second reactor.

Aqueous sodium hydroxide (very little) is also introduced into the second reactor in order to maintain a constant pH of 6.9 (control of addition by pH meter). The reaction mass is then pumped from the second reactor into a liquid-liquid extractor, in which the salt-containing aqueous phase is separated continuously from the product. The product is then spray dried and clarified by filtration, to give a viscous liquid consisting of a mixture of 30 mole % of 2-ethylhexyl mono-n-octyltin tristhioglycolate and 70 mole % of 2-ethylhexyl di-n-octyltin bisthioglycolate. The yield is 98% of theory, based on the two starting mono- and dioctyltin chlorides.

Analysis: Sn (theory): 15.5%; S: 9.0%; Sn (found): 15.2%; S: 8.9%.

EXAMPLE 2

100 parts by weight of mono-n-butyltin trichloride and 307 parts by weight of tetradecyl thioglycolate are pumped continuously at a temperature of 30° C. into a reactor system comprising a cascade of two reactors each equipped with stirrer, level meter, pH meter and thermometer. Aqueous sodium hydroxide is introduced into the first reactor (control of addition by pH meter) such that a pH of about 5 is kept therein. The reaction mass is then pumped into the second reactor, the volume being controlled by the level meter. Feed and discharge are so controlled that the dwell time of the reaction mass in the first reactor is 2 minutes. The heat of reaction is removed so that the temperature in the first and second reactor does not exceed 50° C.

Aqueous sodium hydroxide is also introduced into the second reactor in order to obtain a constant pH of 5 (control of addition by pH meter). The reaction mass is pumped from the second reactor into a continuously operating liquid-liquid extractor which separates the aqueous phase from the product phase. The product phase is then spray dried and clarified by filtration, affording a viscous liquid of the formula n—$C_4H_9Sn(SCH_2COOC_{14}H_{29})_3$. The yield is 96% of theory, based on the starting mono-n-butyltin trichloride.

Analysis: Sn (theory): 11.4%; S: 9.3%; Sn (found): 11.2%; S: 9.1%.

EXAMPLE 3

A previously prepared mixture of 100 parts by weight of di-n-octyltin dichloride and 98 parts by weight of 2-ethylhexyl thioglycolate is pumped continuously at room temperature into a reactor system comprising a cascade of two reactors each equipped with stirrer, level meter, pH meter and thermometer. Simultaneously, aqueous sodium hydroxide solution is added, with efficient stirring, to the reaction mass such that a pH of 6.5 to 7.0 is maintained in the first reactor. The addition of sodium hydroxide is controlled by the pH meter in the first reactor. The heat of reaction liberated during the reaction is not removed. The reaction temperature is 65° C. (The temperature is determined by the adiabatic mode of operation and is dependent on the temperature of the starting mixture of dioctyltin dichloride and 2-ethylhexyl thioglycolate). The reaction mass is then pumped into the second reactor (volume control by the level meter). Feed and discharge of the reaction mixture are so controlled that the dwell time of the reaction mass in the first reactor is 5 minutes.

Aqueous sodium hydroxide solution (very little) is also introduced into the second reactor in order to maintain a constant pH of 6.9 (control of addition by pH meter). The reaction mass is then pumped from the second reactor into a liquid-liquid extractor, in which the salt-containing aqueous phase is separated continuously from the product. The product is subsequently spray dried and clarified by filtration, affording a viscous liquid consisting of 2-ethylhexyl di-n-octyltin bis-thioglycolate. The yield is 97% of theory, based on the starting di-n-octyltin dichloride.

Analysis: Sn (theory): 15.8%; S: 8.5%; Sn (found): 15.7%; S: 8.3%.

What is claimed is:

1. A process for the production of alkyltin thiocarboxylic acid esters from alkyltin halides and thiocarboxylic acid esters in the presence of an acid acceptor, which process comprises carrying out the reaction continuously in a reaction system comprising 2 to 5 agitator vessels with an average dwell time of 1 to 60 minutes, at a constant pH value in the range from 3 to 8, and in a temperature range from 40° to 80° C.

2. A process according to claim 1, wherein the reaction system consists of two reaction vessels.

3. A process according to claim 1, wherein the reaction is carried out in the reaction system with a dwell time of 1 to 10 minutes.

4. A process according to claim 1, wherein the reaction is carried out in the reaction system at a pH from 5 to 7.

5. A process according to claim 1, wherein the reaction is carried out in the reaction system in the temperature range from 50° to 60° C.

6. A process according to claim 1, wherein the starting materials are fed into the reaction system at a temperature of 20° to 30° C. and the reaction itself is carried out adiabatically.

7. A process according to claim 1, wherein the reaction is carried out in the absence of an organic solvent.

8. A process according to claim 1, wherein the product drawn off from the reaction system is separated from the aqueous phase and subsequently dried.

9. A process according to claim 8, wherein the product phase drawn off from the reaction system is separated from the aqueous phase by a continuously operating liquid-liquid extractor or a separating column.

10. A process according to claim 8, wherein the product phase drawn off from the reaction system is separated from the aqueous phase by a continuously operating liquid-liquid centrifugal extractor.

11. A process according to claim 8, wherein the product phase is dried by continuous spray drying or with the aid of a thin-film or falling film evaporator.

12. A process according to claim 1, wherein alkyltin thiocarboxylic acid esters of the formula $$R_xSn[S(CH_2)_nCOOR']_{4-x}$$

wherein x and n are 1 or 2, R is methyl, butyl, octyl, lauryl or the —$CH_2CH_2COO$—n—$C_4H_9$ group, and R' is a $C_8$–$C_{16}$ alkyl group, are prepared from the corresponding alkyltin halides and the corresponding thiocarboxylic acid esters, the term halide denoting chloride, bromide or iodide.

13. A process according to claim 1, wherein alkyltin thiocarboxylic acid esters of the formula $$R_xSn[S(CH_2)_nCOOR']_{4-x}$$

wherein x and n are 1 or 2, R is methyl, butyl, octyl or the —$CH_2CH_2COO$—n—$C_4H_9$ group, and R' is a $C_8$–$C_{16}$ alkyl group, are prepared from the corresponding alkyltin halides and the corresponding thiocarboxylic acid esters, the term halide denoting chloride, bromide or iodide.

* * * * *